(12) United States Patent
Jaffar et al.

(10) Patent No.: US 12,327,642 B2
(45) Date of Patent: Jun. 10, 2025

(54) SYSTEM AND METHOD FOR PROVIDING TELEHEALTH SERVICES USING TOUCHLESS VITALS AND AI-OPTIMIXED ASSESSMENT IN REAL-TIME

(71) Applicant: Veyetals o/a MarkiTech, Oakville (CA)

(72) Inventors: Nauman Jaffar, Oakville (CA); Asif Iqbal, Putrajaya (MY); Farooq Zaman, Kaula Lumpur (MY)

( * ) Notice: Subject to any disclaimer, the term of this patent is extended or adjusted under 35 U.S.C. 154(b) by 158 days.

(21) Appl. No.: 18/111,553

(22) Filed: Feb. 18, 2023

(65) Prior Publication Data
US 2024/0282468 A1    Aug. 22, 2024

(51) Int. Cl.
| | | |
|---|---|---|
| G16H 80/00 | (2018.01) | |
| A61B 5/024 | (2006.01) | |
| G16H 20/10 | (2018.01) | |
| G16H 70/40 | (2018.01) | |

(52) U.S. Cl.
CPC ......... *G16H 80/00* (2018.01); *A61B 5/02416* (2013.01); *G16H 20/10* (2018.01); *G16H 70/40* (2018.01)

(58) Field of Classification Search
None
See application file for complete search history.

(56) References Cited

U.S. PATENT DOCUMENTS

| | | | |
|---|---|---|---|
| 9,924,896 B2 * | 3/2018 | De Haan | A61B 5/7214 |
| 2011/0251493 A1 * | 10/2011 | Poh | G06F 18/2134 |
| | | | 382/128 |
| 2013/0246098 A1 * | 9/2013 | Habboush | G06Q 10/10 |
| | | | 705/3 |
| 2017/0127988 A1 * | 5/2017 | Tao | A61B 5/7257 |
| 2017/0169191 A1 * | 6/2017 | Bowers | G16H 10/60 |
| 2019/0231221 A1 * | 8/2019 | Shin | A61B 5/7278 |
| 2019/0239761 A1 * | 8/2019 | Tao | G06T 5/40 |
| 2020/0397306 A1 * | 12/2020 | Frank | G01J 5/10 |
| 2021/0153752 A1 * | 5/2021 | Park | A61B 5/0205 |
| 2021/0202090 A1 * | 7/2021 | O'Donovan | G16H 15/00 |
| 2021/0369115 A1 * | 12/2021 | Zatvan | A61B 5/1032 |
| 2022/0036878 A1 * | 2/2022 | Cyr | G06F 1/1684 |
| 2022/0142529 A1 * | 5/2022 | Li | A61B 5/681 |
| 2023/0036114 A1 * | 2/2023 | Whitehill | A61B 5/6898 |
| 2023/0063221 A1 * | 3/2023 | Marks | A61B 5/1176 |
| 2023/0293113 A1 * | 9/2023 | Sehgal | G16H 50/20 |

* cited by examiner

*Primary Examiner* — Stella Higgs (57) ABSTRACT

The disclosure provides a method for providing telehealth services using touchless health vitals and artificial intelligence optimized assessment in real-time. The method includes obtaining real-time video and audio data of a user through a video capturing unit. Health vital signs data of the user are obtained from the real-time video and audio data using a touchless vital monitoring module. A real-time voice tone analysis is performed using a trained data model to identify a plurality of factors associated with the voice of the user and a health condition is determined based on comparing the plurality of factors with a predefined threshold associated with historic conversion data of the user. Health insights for the user are derived based on the health vital signs data and the health condition of the user. The health insights are used by the health care professional for further diagnosis and treatment for the user.

19 Claims, 6 Drawing Sheets

SYSTEM AND METHOD FOR PROVIDING TELEHEALTH SERVICES USING TOUCHLESS VITALS AND AI-OPTIMIXED ASSESSMENT IN REAL-TIME

BACKGROUND

Technical Field

Embodiments of this disclosure generally relate to a system and a method for monitoring users' health and more particularly, to a system and method for providing telehealth services by performing touchless health vital signs monitoring and obtaining health insights for the user using emotion artificial intelligence.

Description of the Related Art

Telehealth is the use of digital information and communication technologies to remotely access health care services. Telehealth overcomes challenges of health service delivery primarily due to time and distance enabling better access during emergencies. Telehealth provides convenience, improves care and reduces hospitalization rates. Telehealth care support is gaining importance nowadays as the rising incidence of chronic diseases has increased care demand, necessitating longer interactions between patients and providers. In recent days, the risk of infection and surging demands on the healthcare system due to pandemics such as COVID-19 have made telehealth a safe and necessary tool for disease management. Recent advances in artificial intelligence (AI) and machine learning play a major role in the delivery of health care remotely including the use of tele-assessment, tele-diagnosis, tele-interactions, and tele-monitoring. Applying advanced AI systems in treatment plan optimization and modality can improve outcomes in health and disease management. Further, AI in the last few years has begun to play a highly supportive role to doctors when analyzing the evidence for diagnosing a potential disease. Some of the disadvantages associated with the existing telehealth system include the lack of a full range of appropriate sensors, available bandwidth, network coverage, and the costs of data transmission via public networks. Further, telemonitoring produces a large amount of data that requires accurate analysis for designing an appropriate treatment plan.

There remains a need for a new system and method for passive monitoring and Augmented Reality integrated telemedicine for healthcare professionals to diagnose and recommend an appropriate treatment plan. The present invention is directed toward providing such a system and method for providing telehealth services using passive monitoring and artificial intelligence based health assessment.

SUMMARY

According to the first aspect of the invention, a system for providing telehealth services using touchless health vital signs and artificial intelligence optimized assessment obtained in real-time is provided. The system includes a storage device and a processor that retrieves machine-readable instructions from the storage device. The processor obtains real-time video and audio data of a user as the user is communicating with a health care professional through a video capturing unit. The captured video and audio data of the user and the user identification information are transmitted to a centralized healthcare database that interacts with an Electronic Medical Record system. The processor obtains health vital signs data of the user from the real-time video and audio data using a touchless vital monitoring module. The processor performs a real-time voice tone analysis of the user from the audio data using a trained data model to identify a plurality of factors associated with the voice of the user. The processor determines a health condition of the user based on comparing the plurality of factors with a predefined threshold associated with the historic conversion data of the user. The historic conversion data is stored in the trained data model. The processor derives health insights for the user based on the health vital signs data obtained by the touchless vital monitoring module and the health condition of the user determined using the trained data model. The health insights are used by the health care professional for further diagnosis and treatment for the user.

According to an embodiment, the touchless vital monitoring module obtains the health vital signs data with an optical measurement method using remote-photoplethysmography (rPPG).

According to another embodiment, the health vital signs data of the user are obtained using at least one of commercial off-the-shelf (COTS) health vital signs data obtaining devices, an application program interface or third-party server.

According to yet another embodiment, the obtained health vital signs data of the user are communicated to the processor using a wired or wireless protocol.

According to yet another embodiment, the video capturing unit comprises a high-definition camera or an infrared camera provided with a microphone to capture the real-time video and audio data of the patient using video conferencing tools.

According to yet another embodiment, the health vital signs data include heart rate, heart rate variability, oxygen saturation, respiratory rate, glucose, blood pressure and stress.

According to yet another embodiment, the plurality of factors includes energy of the voice, mood and pitch of the user during speech, slurred or broken speech, type of language, way of word delivery.

According to yet another embodiment, the health condition of the user includes emotional state, stress, sanity and risk matrix.

According to yet another embodiment, the system facilitates the healthcare professional to communicate with multiple users at a time through an interface.

According to yet another embodiment, the processor is configured to identify keywords used by the user in real-time from the video and audio data using a natural language processing (NLP) technique and map the keywords with predefined treatment options and medications to provide recommendations to the healthcare professional for further diagnosis and treatment of the user.

According to yet another embodiment, the processor is configured to convert speech into text in real-time using natural language processing (NLP) technique to generate a chat window for conversation between the user and the health care professional.

According to yet another embodiment, the processor is further configured to communicate with a Drug Database to recommend drugs as per a diagnosis based on conversation between the healthcare professionals using the natural language processing (NLP) technique.

According to the second aspect of the invention, a method for providing telehealth services using touchless health vital signs data and artificial intelligence optimized assessment obtained in real-time is provided. The method includes obtaining, by a processor, a real-time video and audio data of a user as the user is communicating with a health care professional through a video capturing unit. The captured video and audio data of the user and the user identification information are transmitted to a centralized healthcare database that interacts with an Electronic Medical Record system. The method includes obtaining health vital signs data of the user from the real-time video and audio data using a touchless vital monitoring module. The method includes performing, by the processor, a real-time voice tone analysis of the user from audio data using a trained data model to identify a plurality of factors associated with the voice of the user. The method includes determining, by the processor, a health condition of the user based on comparing the plurality of factors with a predefined threshold associated with a historic conversion data of the user. The historic conversion data is stored in the trained data model. The method includes deriving, by the processor, health insights for the user based on the health vital signs data obtained by the touchless vital monitoring module and the health condition of the user determined using the trained data model. The health insights are used by the health care professional for further diagnosis and treatment for the user.

According to an embodiment, the touchless vital monitoring module obtains the health vital signs data with an optical measurement method using remote-photoplethysmography (rPPG).

According to another embodiment, the health vital signs data of the user are obtained using at least one of commercial off-the-shelf (COTS) health vital signs data obtaining devices, an application program interface or third-party server.

According to yet another embodiment, the obtained health vital signs data of the user are communicated to the processor using a wired or wireless protocol.

According to yet another embodiment, the video capturing unit comprises a high-definition camera or an infrared camera provided with a microphone to capture the real-time video and audio data of the patient using video conferencing tools.

According to yet another embodiment, the health vital signs data include heart rate, heart rate variability, oxygen saturation, respiratory rate, glucose, blood pressure and stress.

According to yet another embodiment, the plurality of factors includes energy of the voice, mood and pitch of the user during speech, slurred or broken speech, type of language, way of word delivery.

According to yet another embodiment, the health condition of the user includes emotional state, stress, sanity and risk matrix.

According to yet another embodiment, the method facilitates the healthcare professional to communicate with multiple users at a time through an interface.

According to yet another embodiment, the method further includes identifying keywords used by the user in real-time from the video and audio data using a natural language processing (NLP) technique and map the keywords with predefined treatment options and medications to provide recommendations to the healthcare professional for further diagnosis and treatment of the user.

According to yet another embodiment, the method further includes converting speech into text in real-time using natural language processing (NLP) technique to generate a chat window for conversation between the user and the health care professional.

According to yet another embodiment, the processor is further configured to communicate with a Drug Database to recommend drugs as per a diagnosis based on conversation between the healthcare professionals using the natural language processing (NLP) technique.

According to the third aspect of the invention, a non-transitory computer program product having embodied thereon a computer program for providing telehealth services using touchless health vital signs data and artificial intelligence optimized assessment obtained in real-time is provided. The computer program product storing instructions for: obtaining, by a processor, real-time video and audio data of a user as the user is communicating with a health care professional through a video capturing unit, the captured video and audio data of the user and the user identification information is transmitted to a centralized healthcare database that interacts with an Electronic Medical Record system, obtaining health vital signs data of the user from the real-time video and audio data using a touchless vital monitoring module, performing, by the processor, a real-time voice tone analysis of the user from the audio data using a trained data model to identify a plurality of factors associated with the voice of the user, determining, by the processor, a health condition of the user based on comparing the plurality of factors with a predefined threshold associated with a historic conversion data of the user, the historic conversion data is stored in the trained data model and deriving, by the processor, health insights for the user based on the health vital signs data obtained by the touchless vital monitoring module and the health condition of the user determined using the trained data model, the health insights are used by the health care professional for further diagnosis and treatment for the user.

The system and method of the present invention provide telehealth services based on real-time health analytics that combines insight from historical information with current data, making it easier to conduct a deeper and more comprehensive treatment for the user. The system and method of the present invention facilitate the healthcare industry to deliver proactive care, improving health outcomes, reducing hospital readmissions and improving all-around efficiency through artificial intelligence optimized assessment in real-time.

BRIEF DESCRIPTION OF THE DRAWINGS

The embodiments herein will be better understood from the following detailed description with reference to the drawings, in which.

DETAILED DESCRIPTION OF PREFERRED EMBODIMENTS

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a step" includes single or plural steps and is considered equivalent to the phrase "comprising at least one step." The term "or" refers to a single element of stated alternative elements or a combination of two or more elements, unless the context clearly indicates otherwise. As used herein, "comprises" means "includes." Thus, "comprising terpenes", means "including terpenes", without excluding additional elements. All references, including journal articles, patents, and patent publications cited herein are incorporated by reference in their entirety as if each individual journal article, patent, or patent publication, was specifically and individually indicated to be incorporated by reference in its entirety for all purposes.

Figure 1:
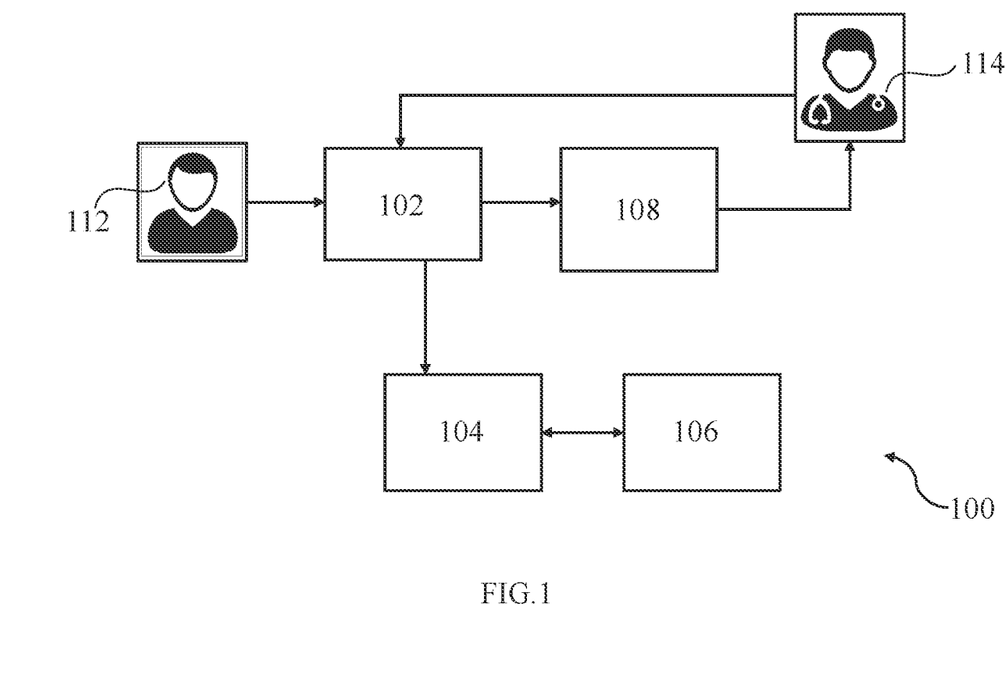
FIG. 1 illustrates a system for providing telehealth services using touchless health vital signs data and artificial intelligence optimized assessment in real-time according to some embodiments herein.

FIG. 1 illustrates a system for providing telehealth services using touchless health vital signs data and artificial intelligence optimized assessment in real-time according to some embodiments herein. The system 100 includes a video capturing unit 102, a centralized healthcare database 104, an EMR system 106, a processor 108 including a touchless vital signs data obtaining module 110 (not shown). The processor 108 is configured to obtain real-time video and audio data of a user 112 as the user 112 is communicating with a health care professional 114 through the video capturing unit 102. The captured video and audio data of the user 112 and the user identification information are transmitted to the centralized healthcare database 104 that interacts with the Electronic Medical Record (EMR) system 106. The user 112 may be identified using face recognition. The processor 108 obtains health vital signs data of the user 112 from the real-time video and audio data using the touchless vital signs data obtaining module 110. The health vital signs data of the user 112 is captured upon receiving permission from the user 112 by the touchless vital signs data obtaining module 110. The processor 108 performs a real-time voice tone analysis of the user 112 from the audio data using a trained data model to identify a plurality of factors associated with the voice of the user 112. The processor 108 determines a condition of the user 112 based on comparing the plurality of factors with a predefined threshold associated with a historic conversion data of the user 112. The historic conversion data is stored in the trained data model. The processor 108 generates health insights for the user 112 based on the health vital signs data obtained by the touchless vital signs data obtaining module 110 and the health condition of the user 112 determined using the trained data model. The health insights are used by the health care professional 114 for further diagnosis and treatment for the user 112. The video capturing unit 102 may be a smartphone, tablet, TV, laptop/desktop capable of capturing high-definition video of the user 112. The video capturing unit 102 may be a high-definition camera or an InfraRed Camera. The high-definition camera or the infrared camera is provided with a microphone to capture the real-time audio data of the patient using video conferencing tools. The microphone may be a multi-dimensional microphone. The real-time video and audio data captured by the video capturing unit 102 is transmitted to the processor 108 using edge computing technologies that ensures high bandwidth transmission with low latency. The touchless vital signs data obtaining module 110 captures the health vital signs data with an optical measurement method using remote-photoplethysmography (rPPG) that monitors the change in blood volume by capturing pixel intensity changes from the skin to measure pulse rate. The method of capturing health vital signs data using remote-photoplethysmography (rPPG) includes detecting the face of the user 112 in the captured video and audio data and modeling to determine facial landmarks and head orientation. A region of the face where most of the blood vessels are concentrated, is selected as the region of interest. The region of interest may further be divided into smaller regions and parallel processing is performed on each region. In the end, higher reliability region results are selected based on the analysis. Signal extraction is performed by measuring an average of each pixel colors (i.e.) red, green, blue of the region over time. For averaging cases, two types of averaging are utilized. one is an average over the sub-region and the other is the moving average over time. Signal filtration is performed by detecting noise from the head motions by fitting the facial model. By detecting peaks, inter-beat intervals are measured and then the heart rates and heart rate variability are estimated. Respiratory Rate (RR) is computed by using the Power Spectral Density (PSD) of the selected Blood Volume Pulse (BVP) signal, in which the frequencies in the range of 0.15-0.35 Hz are retained with a bandpass filter specifically to eliminate cardiac component, and the resultant single peak times 60 provide the estimated RR value. O2 Saturation (SpO2) is computed by utilizing the AC and DC of the signals from the red (R) and blue (B) color channels. The absorbance of Red (R) light and Infrared (IR) light by the pulsatile blood changes with the degree of oxygenation [i.e. arterial blood with more oxygen provides an Alternating Current (AC) signal and venous blood with a low oxygen level provides a Direct Current (DC) signal]. The pixel intensities of two different light sources with respective wavelengths are used to calculate O2 saturation. Stress is indicated by the Heart Rate (HR) value. Table 1 depicts the stress index based on Heart Rate.

TABLE 1

| Heart Rate (bpm) | Stress |
| --- | --- |
| <67 | Relaxed |
| 67-75 | Normal |
| 75-83 | Low |
| 84-91 | Medium |
| 92-100 | High |
| 101-109 | Very high |
| >109 | Extreme |

Blood Pressure (BP) is estimated using a deep learning model in which, the BVP signal is extracted from two different datasets: Finger Video-BP and FaceVideo-BP. The input to the model were the normalized temporal and frequency domain features extracted from the BVP signal, further providing SBP (Systolic Blood pressure) and DBP (Diastolic Blood pressure) as the output signal. Glucose level is estimated using a pre-trained model in which the PPG signals are extracted from the real-time video data of the user 112. The obtained PPG signals are pre-processed and cleaned and provided as input to the pre-trained model to categorize the glucose levels of the user 112 into various severity-level groups. The Glucose level obtained is an absolute instantaneous glucose level of the user 112.

The health vital signs data of the user 112 may be obtained using a four-dimensional radar device. The four-dimensional radars detect the health vital signs based on the modulation effect of a radio signal sent by a transceiver towards the user 112. The health vital signs data may be captured using both remote-photoplethysmography (rPPG) using the real-time high-definition images from the video and audio data and the four-dimensional radar device. The health vital signs data of the user 112 may be obtained using Photoplethysmography (PPG) that uses a light source and a photodetector at the surface of skin to measure the volumetric variations of blood circulation. Photoplethysmography (PPG) sensor monitors changes in the light intensity via reflection from or transmission through the tissue. The changes in light intensity are associated with small variations in blood perfusion of the tissue and provide information on the cardiovascular system. The health vital signs data of the user 112 may be obtained using at least one of commercial off-the-shelf (COTS) health vital signs data obtaining devices, an application program interface or third-party server. The commercial off-the-shelf (COTS) devices includes Oximeters, Blood pressure monitors, Patient Monitoring systems, Vital Sign Devices, Glucose Monitoring Devices, Continuous Glucose monitoring devices, heart monitoring machines, respiratory monitoring systems, heart rate, and heart rate variability monitoring devices. The health vital signs data of the user 112 obtained using the commercial off-the-shelf (COTS) devices are communicated to the processor 108 using a wired or wireless protocol. The vital signs include heart rate, heart rate variability, oxygen saturation, respiratory rate, glucose, blood pressure and stress. The real-time video and audio data of the user 112 is obtained using video conferencing tools like zoom, Microsoft teams via Application Programming Interface using the video capturing unit 102. The vital signs of the user 112 are communicated to the processor 108 using a wired or wireless protocol like wi-fi. The video capturing unit 102 comprising the High-Definition cameras are installed in each room of a hospital and connected to monitor or television screen to connect the user 112 and the health care professional 114 during a video conference. The healthcare professional may communicate with multiple users at a time. The processor 108 performs a real-time voice tone analysis of the user 112 from the audio data using a trained data model to identify a plurality of factors associated with the voice of the user 112. The plurality of factors includes energy of the voice, mood and pitch of the user 112 during speech, slurred or broken speech, type of language, way of word delivery. The processor 108 determines a condition of the user 112 based on comparing the plurality of factors with a predefined threshold associated with the historic conversion data of the user 112. The user condition includes emotional state, stress, sanity and risk matrix. The historic conversion data is stored in the trained data model. The processor 108 performs real-time voice tone analysis to assess the well-being of the user 112. The processor 108 employs machine learning (ML) to analyze the positivity and energy of the voice and analyze the mood and pitch of the speaker/user 112. Positivity is measured by how happy or sad the sound is, and energy is how excited or tired the sound is. The processor 108 identifies other factors like slurred or broken speech, type of language, way of word delivery etc., that help the health care professional 114 to understand the user's condition. A graphical representation of each feeling/emotion is added accordingly after the voice tone analysis. The processor 108 generates health insights for the user 112 based on the health vital signs data obtained by the touchless vital monitoring module and the health condition of the user determined using the trained data model. The health insights are used by the health care professional for further diagnosis and treatment for the user 112. The processor 108 is configured to identify keywords used by the user 108 in real-time from the video and audio data using a natural language processing (NLP) technique and map the keywords with predefined treatment options and medications to provide recommendations to the health care professional 114 for further diagnosis and treatment of the user 112. The processor 108 is configured to convert speech into text in real-time using natural language processing (NLP) technique to generate a chat window for conversation between the user 112 and the health care professional 114. The processor 108 creates smart insights by processing and analyzing large amounts of natural language data (NLP) based on speech and tone of the user 112. The processor 108 picks the keywords used by the user 112 while describing his/her condition. In some embodiments, important points that are relevant to diagnose a particular condition of the user 112 are obtained during the conversation between the user 112 and the health care professional 114 and a summary comprising the most important points is presented to the health care professional 114 using a speech-to-text summarization methodology. In addition, based on the conversation between healthcare professionals, the processor communicates with a Drug Database to recommend drugs as per the suggested diagnosis to the user. Keywords will be mapped with the predefined treatment options and medications. The processor 108 then provides smart health insights and recommendations to the healthcare professional 114 with an option to save them. The health vital signs data of the user 112 may be captured using FDA approved devices and communicate to the processor 108.

Figure 2:
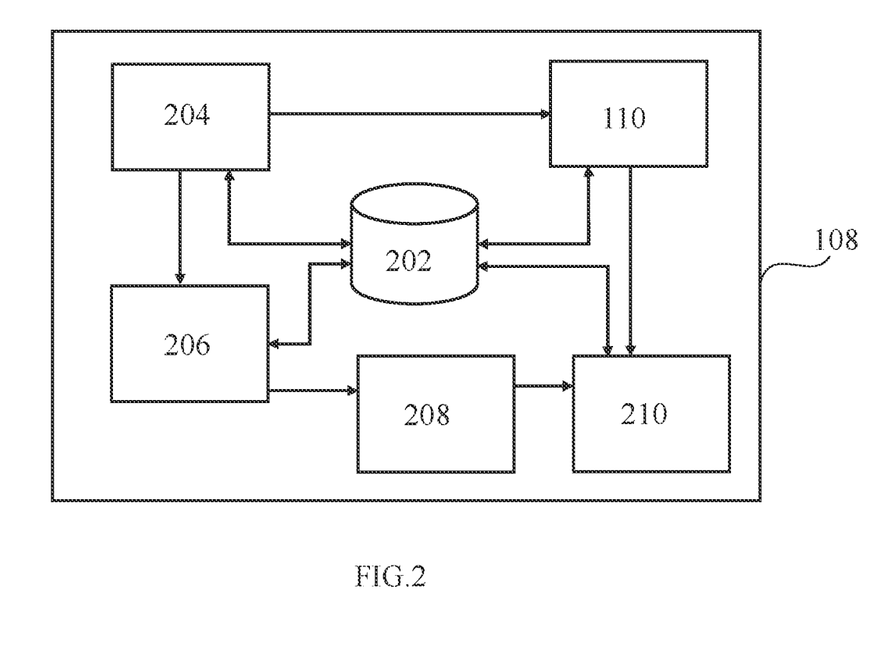
FIG. 2 illustrates a block diagram of the processor including modules for providing telehealth services using touchless health vital signs data and artificial intelligence optimized assessment in real-time according to some embodiments herein.

FIG. 2 illustrates a block diagram of the processor 108 including modules for providing telehealth services using touchless health vital signs data and artificial intelligence optimized assessment in real-time according to some embodiments herein. The processor 108 retrieves machine-readable instructions from a storage device 202. The processor 108 includes a data receiving module 204, touchless vital signs data obtaining module 110, a real-time voice tone analysis module 206, a health condition determination module 208, a health insight deriving module 210. The data receiving module 204 is configured to obtain a real-time video and audio data of a user as the user is communicating with a health care professional through the video capturing unit. The captured video and audio data of the user and the user identification information is transmitted to the centralized healthcare database that interacts with the EMR system. The touchless vital signs data obtaining module 110 is configured to obtain vital signs of the user from the real-time video and audio data using a sensing unit. The real-time voice tone analysis 206 is configured to perform a real-time voice tone analysis of the user from the audio data using a trained data model to identify a plurality of factors associated with the voice of the user. The health condition determination module 208 is configured to determine the user condition based on comparing the plurality of factors with a predefined threshold associated with a historic conversion data of the user stored in the trained data model. The health insight deriving module 210 is configured to generate the health insights for the user based on the health vital signs data obtained by the touchless vital monitoring module and the health condition of the user determined using the trained data model and the health metrics are used by the health care professional for further diagnosis and treatment of the user. The vital signs include heart rate, heart rate variability, oxygen saturation, respiratory rate, glucose, blood pressure and stress. The plurality of factors includes energy of the voice, mood and pitch of the user during speech, slurred or broken speech, type of language, way of word delivery. The health condition of the user includes emotional state, stress, sanity and risk matrix.

Figure 3:
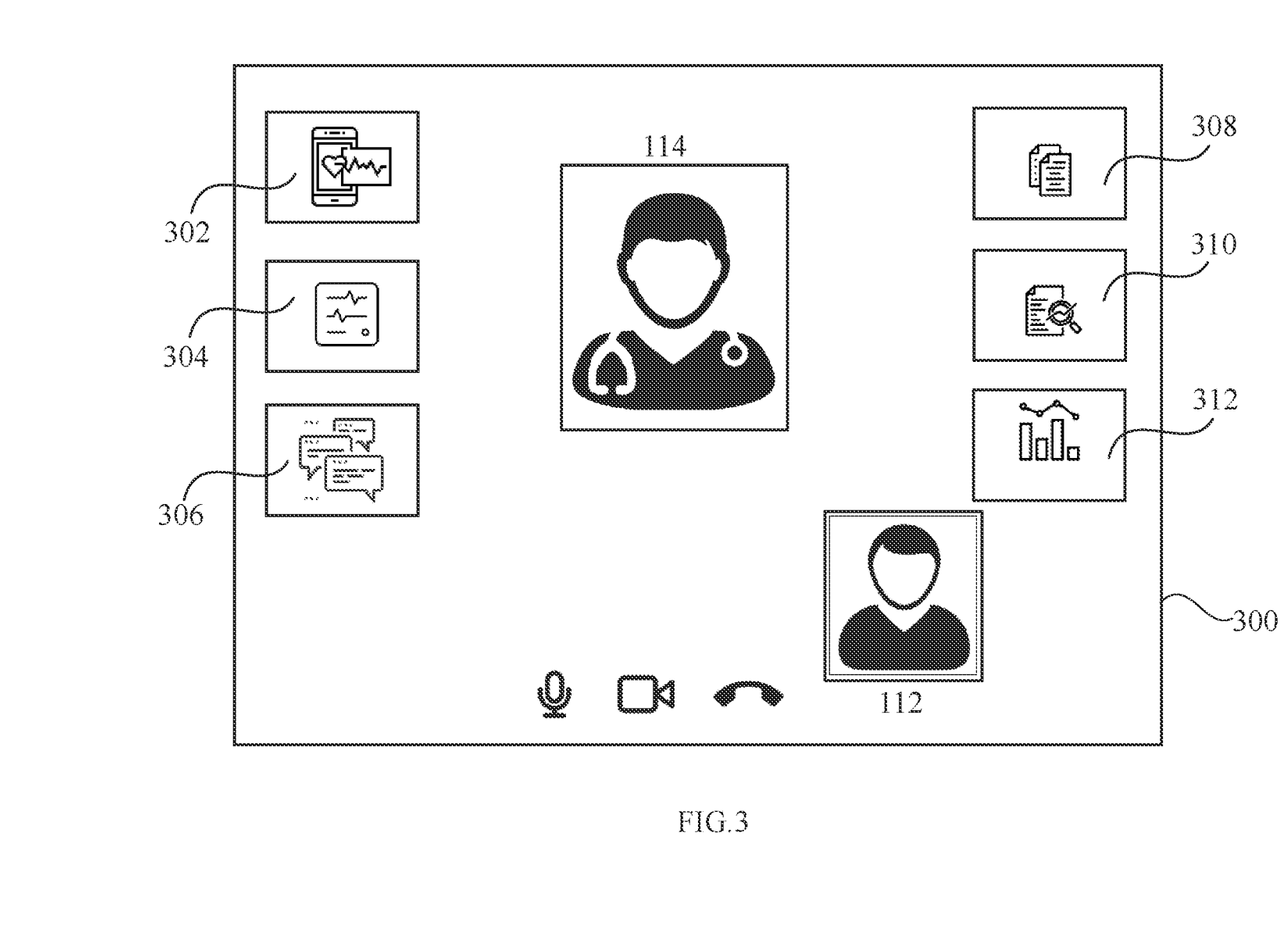
FIG. 3 illustrates a sample graphical user interface of the system for providing telehealth services using touchless health vital signs data and artificial intelligence optimized assessment in real-time according to some embodiments herein.

FIG. 3 illustrates a sample graphical user interface of the system 100 for providing telehealth services using touchless health vital signs data and artificial intelligence optimized assessment obtained in real-time according to some embodiments herein. The graphical user interface 300 shows the touchless health vital signs data 302 obtained by the touchless vital signs data obtaining module 110 that includes heart rate, heart rate variability, oxygen saturation, respiratory rate, stress, systolic blood pressure, diastolic blood pressure. The graphical user interface 300 shows the health vital signs data 304 obtained by the FDA approved devices that includes heart rate, heart rate variability, oxygen saturation, respiratory rate, systolic blood pressure, diastolic blood pressure. The graphical user interface 300 shows a chat window 306. The processor 108 is configured to convert speech into text in real-time using natural language processing (NLP) technique to generate the chat window for conversation between the user 112 and the health care professional 114. The processor 108 is configured to identify keywords used by the user 112 in real-time from the video and audio data using a natural language processing (NLP) technique and map the keywords with predefined treatment options and medications to provide recommendations to the health care professional 114 for further diagnosis and treatment of the user 112. The graphical user interface 300 shows an infograph 308 of the user 112 that comprises current sleep, average sleep, average steps, body weight and height. The graphical user interface 300 shows health insights 310 of the user 112 derived based on the health vital signs data obtained by the touchless vital signs data obtaining module 110 and the health condition of the user 112 determined using the trained data model. The health insights are used by the health care professional 114 for further diagnosis and treatment for the user 112. The graphical user interface 300 shows a bar graph 312 that shows the emotional state of the user 112 including happy, sad, don't care, inspired, afraid, amused and annoyed.

Figure 4A:
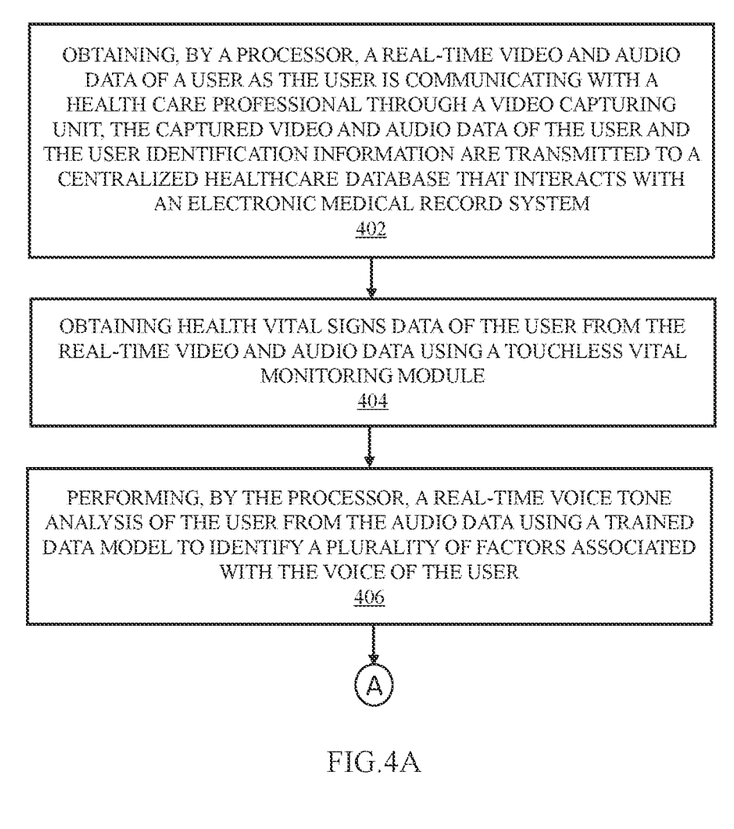
FIGS. 4A-B are flow diagrams that illustrate a method for providing telehealth services using touchless health vital signs data and artificial intelligence optimized assessment obtained in real-time according to some embodiments herein.
Figure 4B:
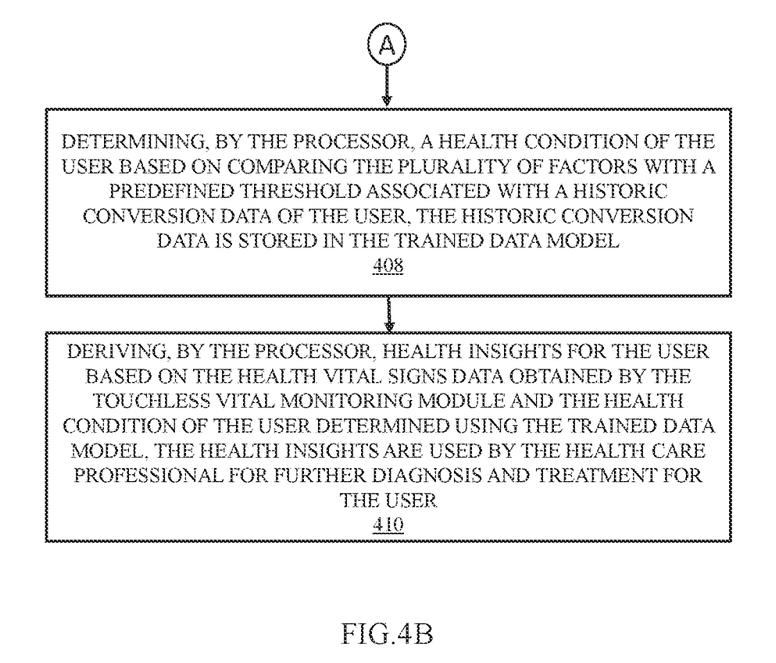

FIGS. 4A-B are flow diagrams that illustrate a method for providing telehealth services using touchless health vital signs data and artificial intelligence optimized assessment obtained in real-time according to some embodiments herein. At a step 402, the method 400 includes obtaining, by a processor, a real-time video and audio data of a user as the user is communicating with a health care professional through a video capturing unit, the captured video and audio data of the user and the user identification information is transmitted to a centralized healthcare database that interacts with an Electronic Medical Record system. At a step 404, the method 400 includes obtaining health vital signs data of the user from the real-time video and audio data using a touchless vital monitoring module. At a step 406, the method 400 includes performing, by the processor, a real-time voice tone analysis of the user from the audio data using a trained data model to identify a plurality of factors associated with the voice of the user. At a step 408, the method 400 includes determining, by the processor a health condition of the user based on comparing the plurality of factors with a predefined threshold associated with a historic conversion data of the user, the historic conversion data is stored in the trained data model. At a step 410, the method 400 includes deriving, by the processor health insights for the user based on the health vital signs data obtained by the touchless vital monitoring module and the health condition of the user determined using the trained data model, the health insights are used by the health care professional for further diagnosis and treatment for the user.

Figure 5:
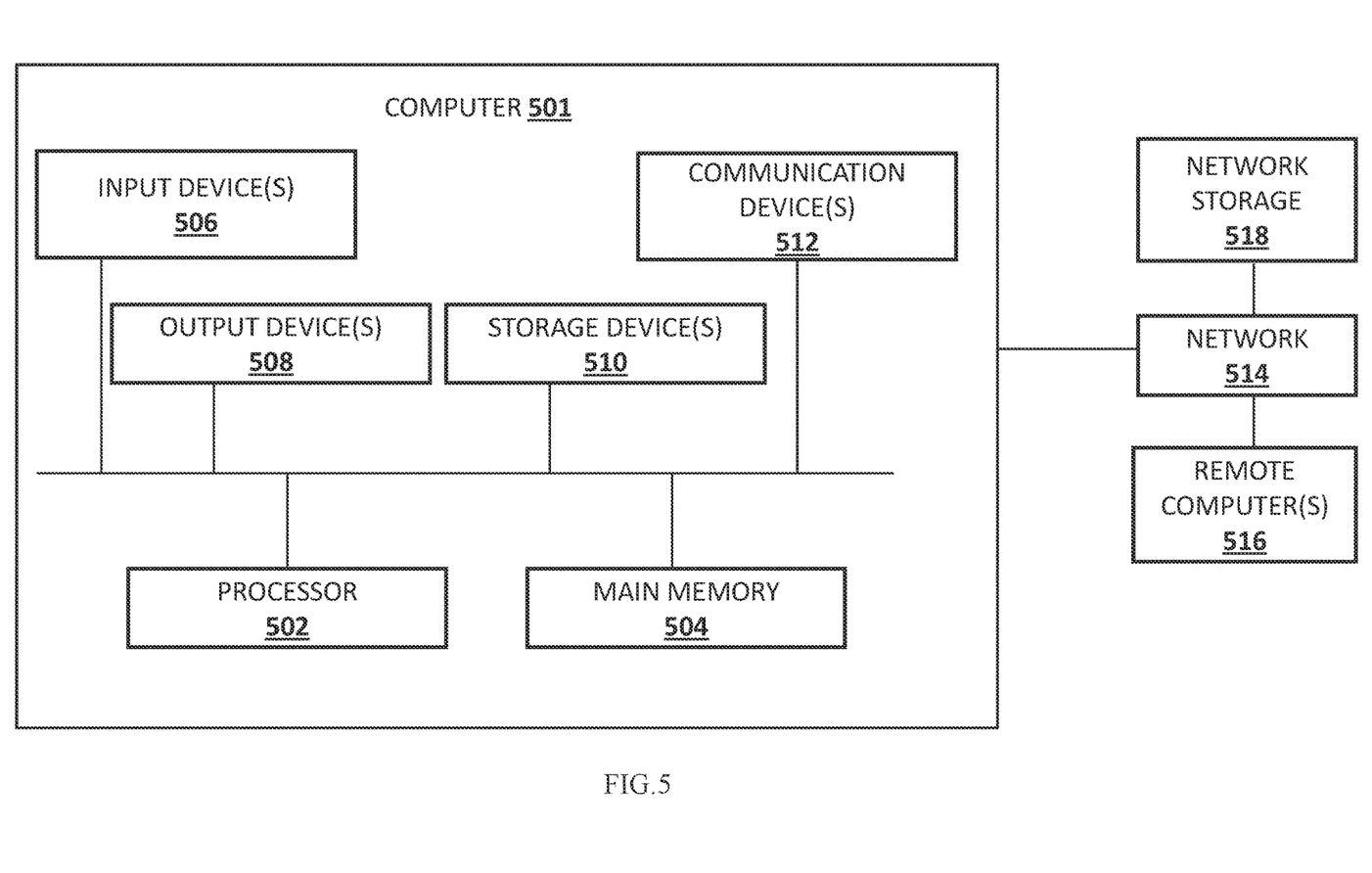
FIG. 5 illustrates a general computer architecture that can be appropriately configured to implement components disclosed in accordance with various embodiments.

FIG. 5 illustrates a general computer architecture 500 that can be appropriately configured to implement components disclosed in accordance with various embodiments. The general computing architecture 500 can include various common computing elements, such as a computer 501, a network 514, and one or more remote computers 516. The computer 501 may be a server, a desktop computer, a laptop computer, a tablet computer or a mobile computing device. The computer 501 may include a processor 502, a main memory 504 and a system bus. The processor 502 may include one or more processing units that can operate independently of each other. The main memory 504 may include volatile devices, non-volatile devices, or other random access memory devices. The computer 501 may include secondary storage 510 that may include one or more removable and/or non-removable storage units that stores an operating system to manages various applications on the computer 501. The secondary storage 510 may also be used to store software configured to implement the components of the embodiments disclosed herein and that may be executed as one or more applications under the operating system. The computer 501 may also include communication device(s) 512 through which the computer communicates with other devices, such as one or more remote computers 516, over wired and/or wireless computer networks 514. The communication device (s) 512 may communicate over Wi-Fi, Bluetooth, and/or mobile telephone networks. The computer 501 may also access network storage 518 through the computer network 514. The network storage 518 may include a network attached storage device or a cloud-based storage. The operating system and/or software may alternatively be stored in the network storage 518. The computer 501 may have various input device(s) 506 for example, keyboard, mouse, touchscreen, camera, microphone, or a sensor. Output device(s) 508 for example, a display, speakers, printer. The storage devices 510, communication device (s) 512, input devices 506 and output devices 508 may be integrated within a computer system or may be connected through various input/output interface devices on the computer.

In closing, it is to be understood that the embodiments of the invention disclosed herein are illustrative of the principles of the present invention. Other modifications that may be employed are within the scope of the invention. Thus, by way of example, but not of limitation alternative configurations of the present invention may be utilized in accordance with the teachings herein. Accordingly, the present invention is not limited to that precisely as shown and described.

What is claimed is:

1. A system for providing telehealth services using touchless health vital signs data and artificial intelligence optimized assessment obtained in real-time, wherein the system comprising:
a storage device; and a processor retrieving machine-readable instructions from the storage device which, when executed by the processor, enable the processor to:

obtain real-time video and audio data of a user as the user is communicating with a healthcare professional through a video capturing unit, wherein the captured video and audio data of the user and user identification information are transmitted to a centralized healthcare database that interacts with an Electronic Medical Record system;

capture health vital signs data of the user from the real-time video and audio data using a touchless vital monitoring module, wherein the touchless vital monitoring module captures the health vital signs data with an optical measurement method using remote-photoplethysmography (rPPG) by selecting a region of a face where most of blood vessels are concentrated as a region of interest from the real-time video, dividing the region of interest into smaller regions, performing parallel processing on each smaller region, selecting higher reliability region from divided smaller regions based on results of parallel processing, extracting signal by measuring an average of each pixel colors of higher reliability each region over time, performing signal filtration by detecting noise from head motions by fitting a facial mode model, and capturing the health vital signs data based on signals extracted from the higher reliability region of interest, wherein capturing the health vital signs data based on signals extracted from the higher reliability region of interest includes (i) estimating heart rate and heart rate variability by measuring inter-beat intervals in peaks in the signals extracted from the higher reliability region of interest, (ii) determining respiratory rate using power spectral density of a selected blood volume pulse signal, (iii) determining $O_2$ saturation by utilizing alternating current and direct current signals from the red and blue color channels, (iv) determining stress level based on the heart rate, and (v) determining blood pressure from the blood volume pulse signal;

perform a real-time voice tone analysis of the user from the audio data using a trained data model to identify a plurality of factors associated with the voice of the user;

determine a health condition of the user based on comparing the plurality of factors with a predefined threshold associated with a historic conversion data of the user, wherein the historic conversion data is stored in the trained data model; and derive health insights for the user based on the health vital signs data obtained by the touchless vital monitoring module and the health condition of the user determined using the trained data model, wherein the health insights are used by the health care professional for further diagnosis and treatment for the user, wherein the processor is further configured to communicate with a Drug Database to recommend drugs to the user as per a diagnosis based on conversation between the healthcare professionals and the user using a natural language processing (NLP) technique.

2. The system of claim 1, wherein the health vital signs data of the user are obtained using at least one of commercial off-the-shelf (COTS) health vital signs data obtaining devices, an application program interface or third-party server.

3. The system of claim 2, wherein the obtained health vital signs data of the user are communicated to the processor using a wired or wireless protocol.

4. The system of claim 1, wherein the video capturing unit comprises a high-definition camera or an infrared camera provided with a microphone to capture the real-time video and audio data of the patient using video conferencing tools.

5. The system of claim 1, wherein the plurality of factors includes energy of the voice, mood and pitch of the user during speech, slurred or broken speech, type of language, way of word delivery.

6. The system of claim 1, wherein the health condition of the user includes emotional state, stress, sanity and risk matrix.

7. The system of claim 1, wherein the system facilitates the healthcare professional to communicate with multiple users at a time through an interface.

8. The system of claim 1, wherein the processor is configured to identify keywords used by the user in real-time from the video and audio data using the natural language processing (NLP) technique, map the keywords with predefined treatment options and medications, and provide recommendations to the health care professional for further diagnosis and treatment of the user.

9. The system of claim 1, wherein the processor is configured to convert speech into text in real-time using natural language processing (NLP) technique to generate a chat window for conversation between the user and the health care professional.

10. A method for providing telehealth services using touchless health vital signs data and artificial intelligence optimized assessment obtained in real-time, wherein the method comprising:

obtaining, by a processor, real-time video and audio data of a user as the user is communicating with a healthcare professional through a video capturing unit, wherein the captured video and audio data of the user and user identification information are transmitted to a centralized healthcare database that interacts with an Electronic Medical Record system;

obtaining health vital signs data of the user from the real-time video and audio data using a touchless vital monitoring module, wherein the touchless vital monitoring module captures the health vital signs data with an optical measurement method using remote-photoplethysmography (rPPG) by selecting a region of a face where most of blood vessels are concentrated as a region of interest from the real-time video, dividing the region of interest into smaller regions, performing parallel processing on each smaller region, selecting higher reliability region from divided smaller regions based on results of parallel processing, extracting signal by measuring an average of each pixel colors of higher reliability each region over time, performing signal filtration by detecting noise from head motions by fitting a facial mode model, and capturing the health vital signs data based on signals extracted from the higher reliability region of interest, wherein capturing the health vital signs data based on signals extracted from the higher reliability region of interest includes (i) estimating heart rate and heart rate variability by measuring inter-beat intervals in peaks in the signals extracted from the higher reliability region of interest, (ii) determining respiratory rate using power spectral density of a selected blood volume pulse signal, (iii) determining $O_2$ saturation by utilizing alternating current and direct current signals from the red and blue color channels, (iv) determining stress level based on the heart rate, and (v) determining blood pressure from the blood volume pulse signal;

performing, by the processor, a real-time voice tone analysis of the user from the audio data using a trained data model to identify a plurality of factors associated with the voice of the user;

determining, by the processor, a health condition of the user based on comparing the plurality of factors with a predefined threshold associated with a historic conversion data of the user, wherein the historic conversion data is stored in the trained data model; and deriving, by the processor, health insights for the user based on the health vital signs data obtained by the touchless vital monitoring module and the health condition of the user determined using the trained data model, wherein the health insights are used by the health care professional for further diagnosis and treatment for the user, wherein the method further comprises communicating with a Drug Database to recommend drugs to the user as per a diagnosis based on conversation between the healthcare professionals and the user using a natural language processing (NLP) technique.

11. The method of claim 10, wherein the health vital signs data of the user are obtained using at least one of commercial off-the-shelf (COTS) health vital signs data obtaining devices, an application program interface or third-party server.

12. The method of claim 11, wherein the obtained health vital signs data of the user are communicated to the processor using a wired or wireless protocol.

13. The method of claim 10, wherein the video capturing unit comprises a high-definition camera or an infrared camera provided with a microphone to capture the real-time video and audio data of the patient using video conferencing tools.

14. The method of claim 10, wherein the plurality of factors includes energy of the voice, mood and pitch of the user during speech, slurred or broken speech, type of language, way of word delivery.

15. The method of claim 10, wherein the health condition includes emotional state, stress, sanity and risk matrix.

16. The method of claim 10, wherein the method facilitates the healthcare professional to communicate with multiple users at a time through an interface.

17. The method of claim 10, wherein the method further comprises identifying keywords used by the user in real-time from the video and audio data using a natural language processing (NLP) technique and map the keywords with predefined treatment options and medications to provide recommendations to the health care professional for further diagnosis and treatment of the user.

18. The method of claim 10, wherein the method further comprises converting speech into text in real-time using the natural language processing (NLP) technique to generate a chat window for conversation between the user and the health care professional.

19. A non-transitory computer program product having embodied thereon a computer program for providing telehealth services using touchless health vital signs data and artificial intelligence optimized assessment obtained in real-time, the computer program product storing instructions, the instructions comprising instructions for:

obtaining, by a processor, real-time video and audio data of a user as the user is communicating with a health care professional through a video capturing unit, wherein the captured video and audio data of the user and the user identification information are transmitted to a centralized healthcare database that interacts with an Electronic Medical Record system;

obtaining health vital signs data of the user from the real-time video and audio data using a touchless vital monitoring module, wherein the touchless vital monitoring module captures the health vital signs data with an optical measurement method using remote-photoplethysmography (rPPG) by selecting a region of a face where most of blood vessels are concentrated as a region of interest from the real-time video, dividing the region of interest into smaller regions, performing parallel processing on each smaller region, selecting higher reliability region from divided smaller regions based on results of parallel processing, extracting signal by measuring an average of each pixel colors of higher reliability each region over time, performing signal filtration by detecting noise from head motions by fitting a facial mode model, and capturing the health vital signs data based on signals extracted from the higher reliability region of interest, wherein capturing the health vital signs data based on signals extracted from the higher reliability region of interest includes (i) estimating heart rate and heart rate variability by measuring inter-beat intervals in peaks in the signals extracted from the higher reliability region of interest, (ii) determining respiratory rate using power spectral density of a selected blood volume pulse signal, (iii) determining $O_2$ saturation by utilizing alternating current and direct current signals from the red and blue color channels, (iv) determining stress level based on the heart rate, and (v) determining blood pressure from the blood volume pulse signal;

performing, by the processor, a real-time voice tone analysis of the user from the audio data using a trained data model to identify a plurality of factors associated with the voice of the user;

determining, by the processor, a health condition of the user based on comparing the plurality of factors with a predefined threshold associated with a historic conversion data of the user, wherein the historic conversion data is stored in the trained data model; and deriving, by the processor, health insights for the user based on the health vital signs data obtained by the touchless vital monitoring module and the health condition of the user determined using the trained data model, wherein the health insights are used by the health care professional for further diagnosis and treatment for the user, wherein the method further comprises communicating with a Drug Database to recommend drugs to the user as per a diagnosis based on conversation between the healthcare professionals and the user using a natural language processing (NLP) technique.

* * * * *

UNITED STATES PATENT AND TRADEMARK OFFICE
CERTIFICATE OF CORRECTION

| | | |
|---|---|---|
| PATENT NO. | : 12,327,642 B2 | Page 1 of 1 |
| APPLICATION NO. | : 18/111553 | |
| DATED | : June 10, 2025 | |
| INVENTOR(S) | : Nauman Jaffar, Asif Iqbal and Farooq Zaman | |

It is certified that error appears in the above-identified patent and that said Letters Patent is hereby corrected as shown below:

On the Title Page

Item (54), change "AI-OPTIMIXED" to read as follows -- AI-OPTIMIZED --.

In the Specification

Column 1, Line 3, change "AI-OPTIMIXED" to read as follows -- AI-OPTIMIZED --.

Signed and Sealed this
Twenty-sixth Day of August, 2025

Coke Morgan Stewart
*Acting Director of the United States Patent and Trademark Office*